US006482167B2

(12) United States Patent
Grim et al.

(10) Patent No.: US 6,482,167 B2
(45) Date of Patent: Nov. 19, 2002

(54) SEALED EDGE ORTHOPAEDIC CASTING TECHNIQUE

(75) Inventors: Tracy E. Grim, Thousand Oaks, CA (US); Joseph M. Iglesias, Thousand Oaks, CA (US); Wendy Henderson, Ventura, CA (US); Michael Campos, Camarillo, CA (US)

(73) Assignee: Royce Medical Product, Camarillo, CA (US)

( * ) Notice: Subject to any disclaimer, the term of this patent is extended or adjusted under 35 U.S.C. 154(b) by 0 days.

(21) Appl. No.: 09/823,968

(22) Filed: Mar. 29, 2001

(65) Prior Publication Data

US 2002/0143282 A1 Oct. 3, 2002

(51) Int. Cl.$^7$ .................................................. A61F 5/00
(52) U.S. Cl. ..................... 602/8; 602/5; 602/6
(58) Field of Search ................ 602/1, 5–6, 8, 602/19, 21, 23, 27–29; 128/882, 892

(56) References Cited

U.S. PATENT DOCUMENTS

| 4,011,596 A | * | 3/1977 | Chang .............................. 2/16 |
| 4,800,872 A | | 1/1989 | Buese et al. ................... 128/90 |
| 4,898,159 A | | 2/1990 | Buese et al. ................... 128/90 |
| 4,905,692 A | * | 3/1990 | More ........................... 606/151 |
| 5,085,917 A | | 2/1992 | Hodnett, III ................ 428/173 |
| 5,308,679 A | | 5/1994 | Saito et al. .................. 428/193 |
| 5,312,669 A | * | 5/1994 | Bedard ......................... 428/105 |
| 5,372,572 A | * | 12/1994 | Tamagni ....................... 602/16 |
| 5,421,811 A | * | 6/1995 | More et al. .................... 602/21 |
| 5,718,966 A | | 2/1998 | Gray et al. .................. 428/193 |
| 5,744,528 A | * | 4/1998 | Callinan et al. ............. 524/265 |
| 5,766,724 A | * | 6/1998 | Tailor et al. ................ 428/110 |
| 5,853,380 A | * | 12/1998 | Miller ........................... 602/27 |
| 5,913,840 A | * | 6/1999 | Allenberg et al. ............. 602/8 |
| 6,030,355 A | * | 2/2000 | Callinan et al. ................ 602/6 |
| 6,042,557 A | * | 3/2000 | Ferguson et al. ............... 602/6 |
| 6,159,877 A | * | 12/2000 | Scholz et al. ............... 442/103 |

* cited by examiner

Primary Examiner—Michael A. Brown
Assistant Examiner—Lalita M Hamilton
(74) Attorney, Agent, or Firm—Oppenheimer Wolff & Donnelly LLP

(57) ABSTRACT

A technique for forming orthopaedic splints or supports includes the steps of impregnating the edges of casting material with non-rigid bonding material and subsequently impregnating the casting material with water hardenable material such as urethane. The edge treatment keeps the edges in a relatively cushioning or non-rigid state to avoid irritation of the skin of the patient. The blanks may be formed using a mold having a groove defining the outline of the casting blank, and a ridge for implementing the impregnation of a bead of bonding material into the casting fabric. The casting blank material may be formed of spacer or double knit type material, or may be formed of several layers of fabric including high strength filaments, and may have padding material as one layer.

48 Claims, 3 Drawing Sheets

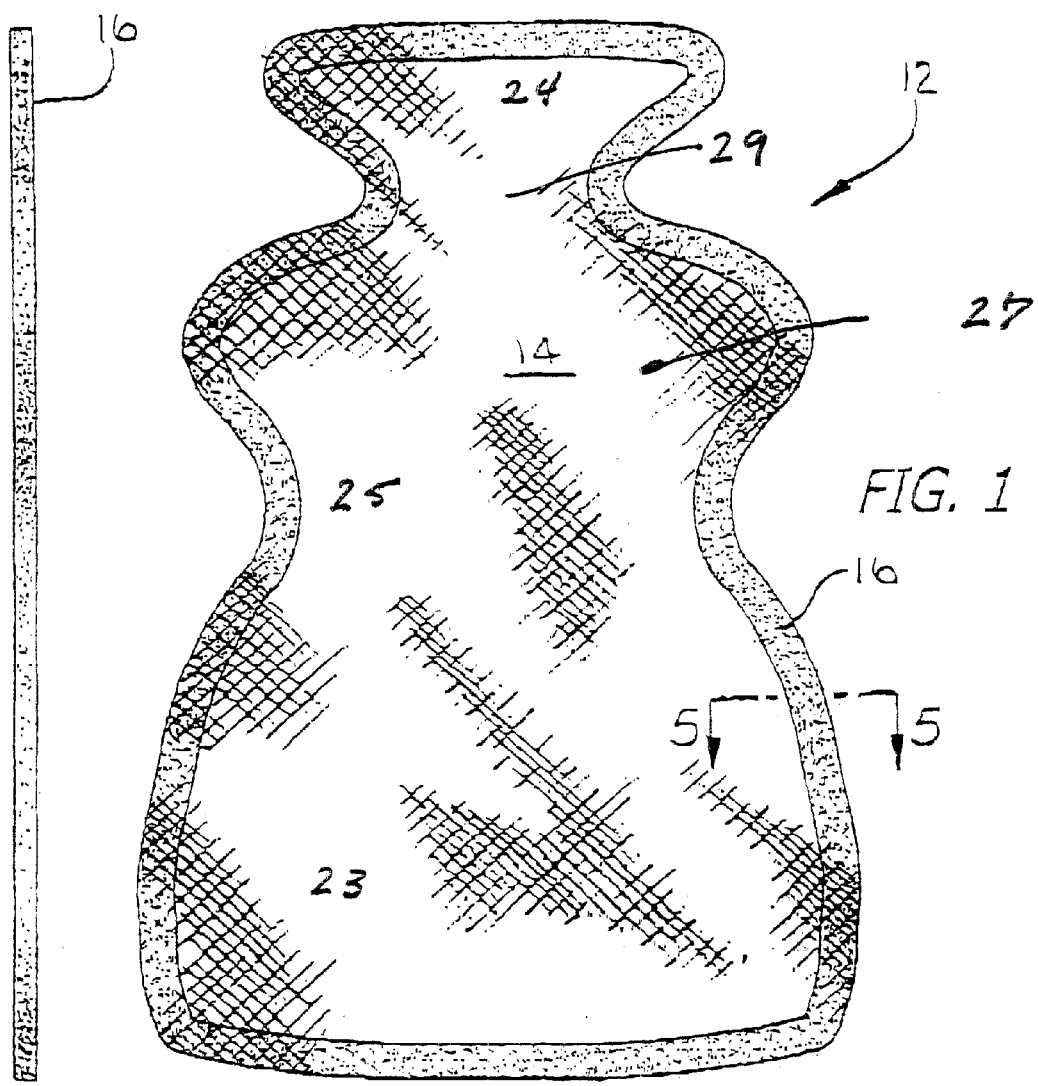

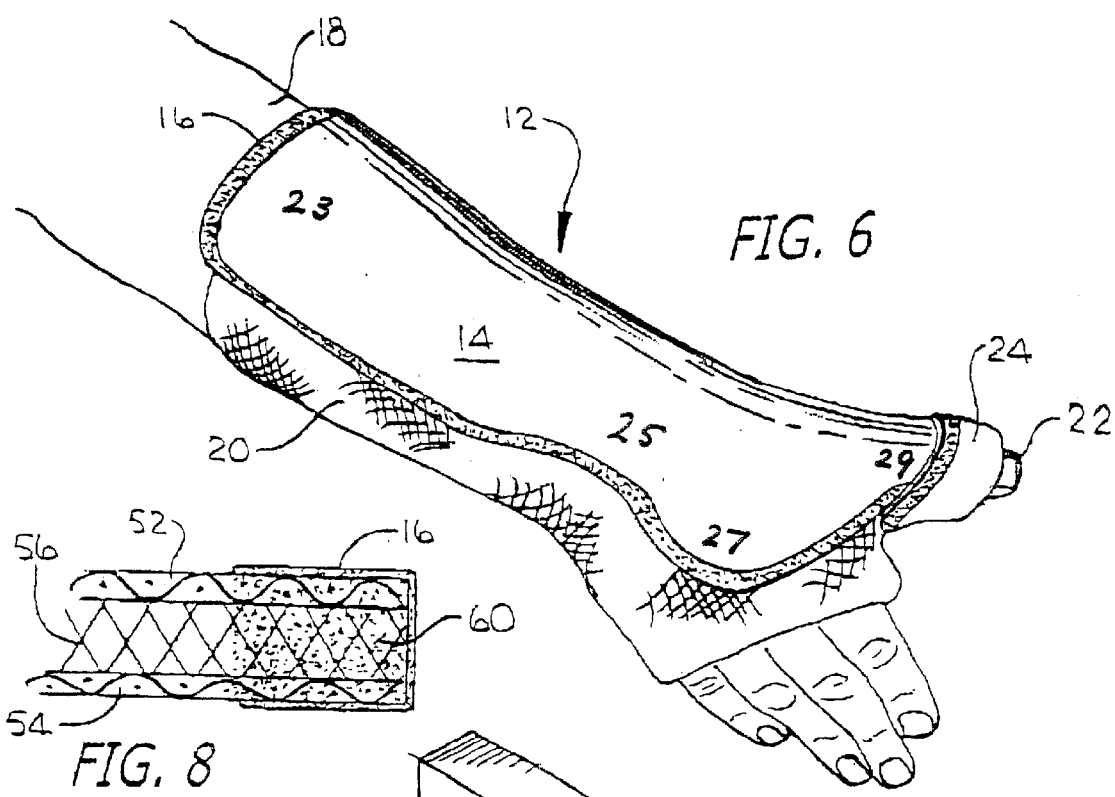
FIG. 6
FIG. 8
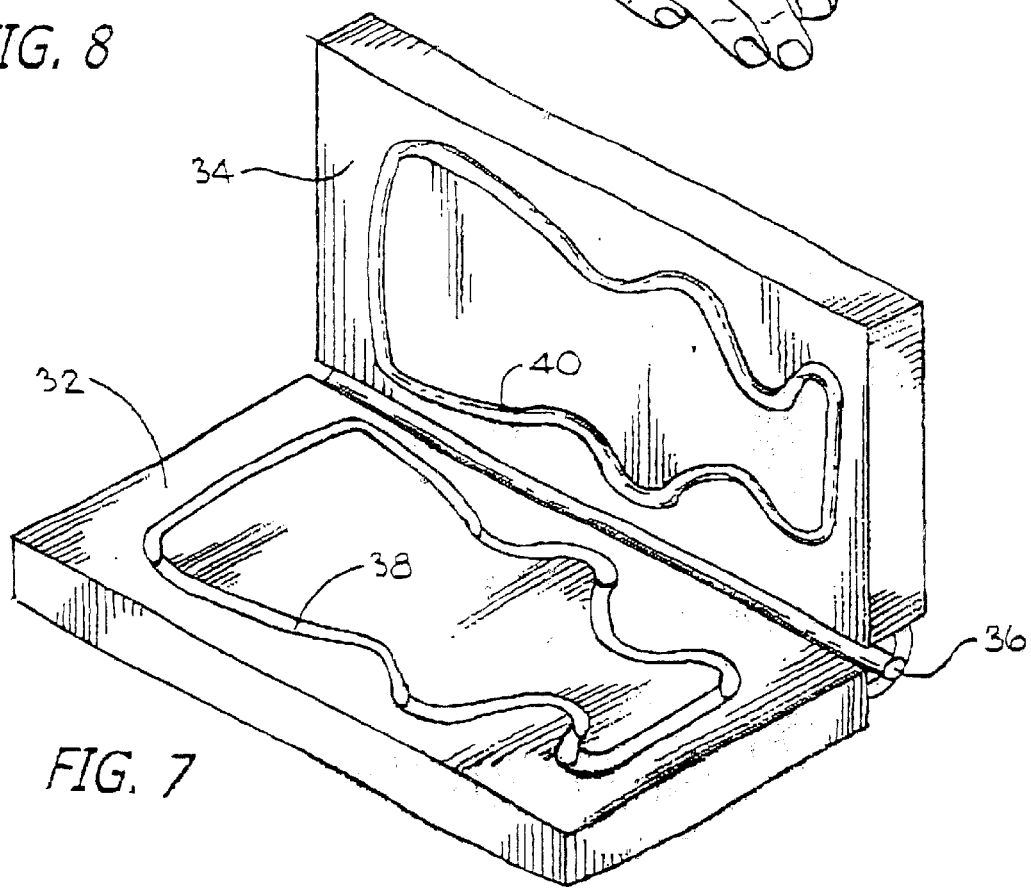
FIG. 7

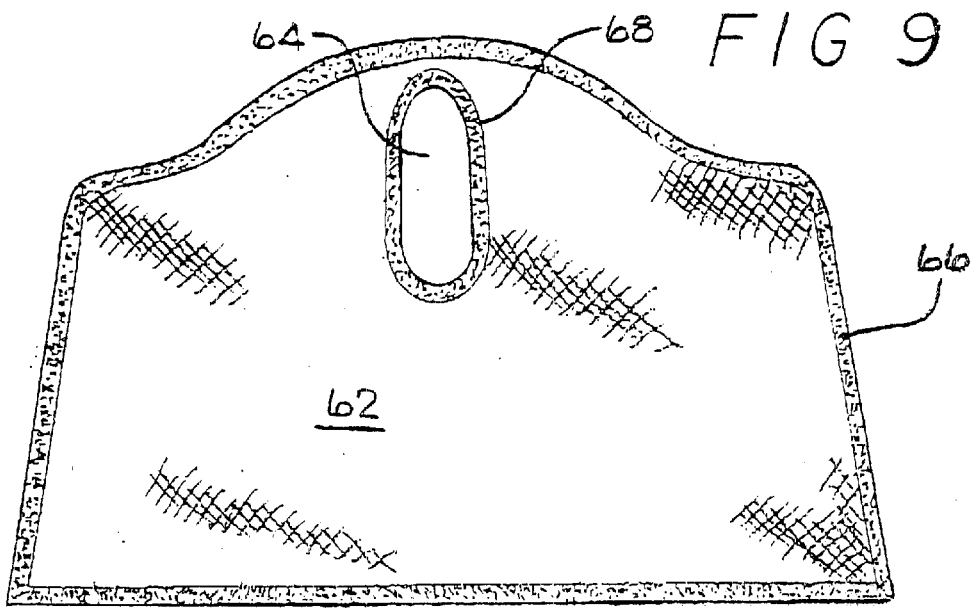
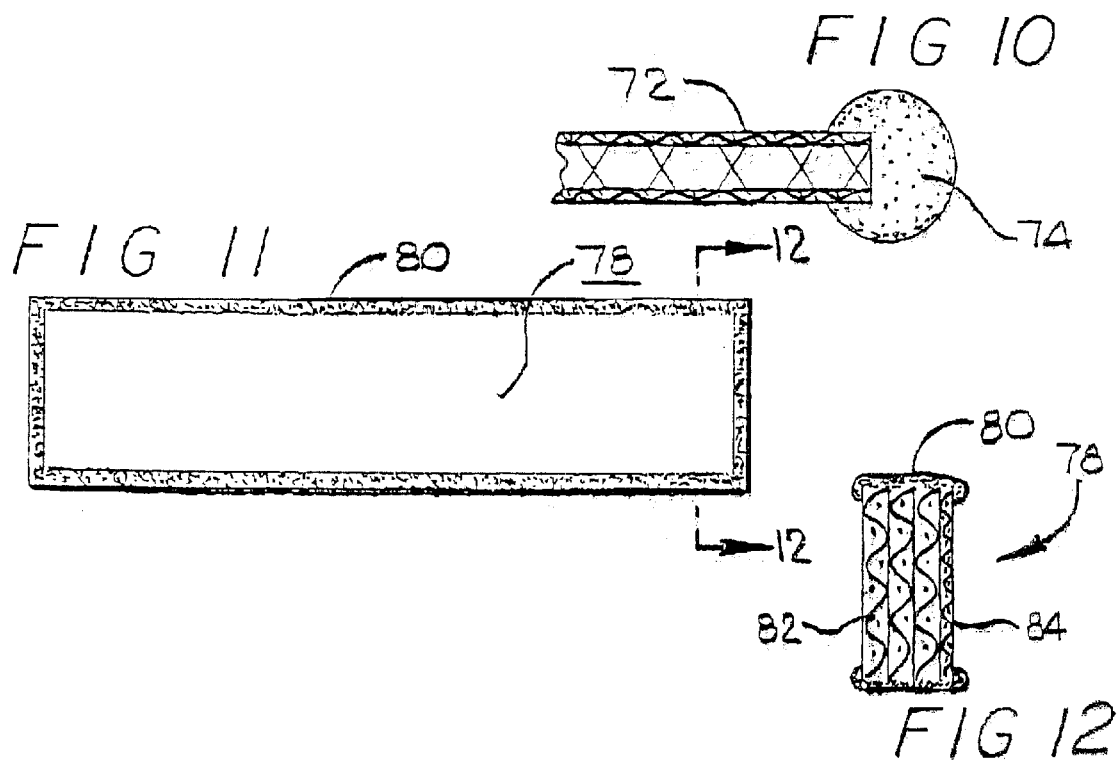

SEALED EDGE ORTHOPAEDIC CASTING TECHNIQUE

BACKGROUND OF THE INVENTION

1. Field of the Invention

This invention relates to casting arrangements for splints or supports.

2. General Background and State of the Art

In the field of orthopaedic immobilization assemblies, such as splints and supports, it is well known to use hardenable material, particularly water hardenable material impregnated into high strength fabric, as a splint or support. In practice, a blank or a tape may be impregnated with a water hardenable urethane. At the time when the splint or support is to be applied to the patient, it is dipped into water, applied to the injured part of the anatomy, and, within a few minutes, hardens.

One troublesome problem which has been encountered involves the edges of the impregnated material, which often have frayed fabric or outwardly extending threads or filaments. These frayed edges or outwardly extending threads or filaments become very rigid and sharp as the urethane hardens; and these sharp edges often irritate and scratch the skin of the patient over the extended period of time that the cast or support is in place.

For completeness, reference is made to U.S. Pat. No. 4,800,872, issued Jan. 31, 1989, which discloses the application of very low concentrations of a binder (not more than 90 grams per square meter) to an orthopaedic casting tape. However, spraying broad areas of the tape with the binder would tend to inhibit impregnation of the water hardenable material; and the very low concentrations of the binder do not provide the edges with the desired level of protection for the patient.

It is also recognized that the edges of materials for non-medical applications have been treated heretofore to prevent raveling. However, in the case of orthopaedic casting blanks or tapes, which are impregnated with water hardenable material, once the water hardenable material has been activated, and the blank has been hardened, there is no problem with raveling. Also, it is important for medical orthopaedic uses that the edge treatment material provide a non-rigid edge and be formed of a material which is compatible with contact with the skin and which is sufficiently soft so that it does not scratch or irritate the skin.

INVENTION SUMMARY

Accordingly, a principal object of the invention is to provide a more comfortable cast or support, with edges which do not cut into or irritate the skin of the patient.

In accordance with one illustrative embodiment of the invention, the edges or ends of a casting blank, strip, or tape are treated or impregnated with a non-rigid, material prior to impregnating the casting fabric with the water hardenable material. The casting material can be either a single or multi-layer fabric including fiberglass and/or other high strength fibers. It is also possible to use multiple layers of a single or double layer fabric, or double knit type spacer material. The non-rigid edge material could be a silicone, a rubber, adhesive material, urethane, or other non-rigid or relatively soft material. Once cured, the flexible material binds the filaments of the casting fabric together, thereby creating a sealed edge which is smooth and comfortable. A preferred type of non-rigid material is one in which, after curing, it does not restrict or mask the beneficial properties (i.e., movement, moldability, etc.) of the casting material. Using certain edge treatments, it is possible to block the water hardenable material from the edges of the cast or splint, creating a type of "flex-edge" feature which will provide further comfort to the user.

In another illustrative embodiment of the invention, a casting blank may be formed in an irregular configuration for application to a particular portion of the anatomy, and some or all edges thereof may be impregnated with a bead of the non-rigid bonding material. The fabric of the casting blank may be "spacer" or double knit type material formed of two spaced layers of knit or woven material with filaments extending between and spacing apart the two layers, and with these filaments being integrally knit or woven into both of the two spaced layers. The casting material may include fiberglass and/or other high strength fibers.

In the formation of the casting blank, and the application of non-rigid bonding material, any of a number of techniques may be used. Thus, the blank may be initially cut to the desired shape, and may thereafter be edge coated with a bead of the preferred non-rigid bonding material. If the bonding material is substantial enough, the edge treatment can extend past the edge of the casting material. One example of this would be a foaming material which would also provide some cushioning. The bonding material may be applied by any number of ways, for example by spraying, brushing, pressing, dipping or the like.

However, because the casting blank is preferably formed of high strength, fairly stiff fibers where the fabric may fray substantially when cut, another method is preferred. This method involves the use of a mold, with two generally flat mating surfaces for receiving a rectangular blank of casting material. One of the two mating surfaces is provided with a groove for receiving the non-rigid cushioning or bonding material, and with the overall configuration of the groove corresponding to the desired outline of the casting blank. The other half of the mold has a mating rib in the same configuration as the groove on the other surface of the mold. In practice, the edge cushioning or treatment material, such as a silicone, rubber, adhesive, urethane, or a non-water hardenable plastic, is applied into the groove, the rectangular casting blank is placed in the mold, and the mold is firmly closed, with the rib forcing the fabric of the casting blank down into the cushioning material so that the rectangular casting blank now has the flexible material impregnated into the fabric in the desired irregular configuration of the final casting blank. After the non-rigid material sets up, either by curing or the evaporation of solvent, the blank is formed by cutting through the sealed area, leaving a non-rigid, non-fraying edge around the periphery of the blank. The irregularly shaped blank is then impregnated with hardenable material. Depending on the bonding material chosen and the method of application, it is possible that only the two surface layers of the edges of the blank will retain any of the bonding material, leaving voids in the inner matrix of the double knit material.

Besides applying the edge treatment to provide comfort around the outer edges of an irregularly shaped blank, the non-rigid bonding material may also be applied to other locations of the casting material, to avoid skin irritation at cutouts through the casting material, and to the longitudinal edges of a strip of casting material, for examples. As an optional advantage, the bonding material may prevent the impregnation of the sealed areas with any water hardenable material giving the eventual support a flexible edge feature. In addition to being useful for sealing the edges of a casting material, the flexible edge material can also be used to secure padding material to one or both sides of the casting material. In practice, before the edge material is applied, the cast material is overlaid with single or multiple layers of a padding type material. The edges are then treated with the non-rigid material which serves to secure all of the layers together.

In the application of the edge treatment to the edges of the casting blank or tape, it is preferably directly applied in a fairly high concentration so that it penetrates and seals the edges but does not extend inwardly over the broad remaining areas of the blank or tape. Preferably the concentration is in the order of at least 400 grams per square meter, up to 10,000 grams per square meter, and preferably between 600 and 3,500 grams per square meter. Normally the edge treatment does not extend inward from the edges for more than one centimeter, or one-quarter inch or one-half inch.

Other objects, features and advantages of the invention will become apparent from a consideration of the following detailed description, and from the accompanying drawings.

BRIEF DESCRIPTION OF THE DRAWINGS

FIG. 1 is a top plan view of a casting blank illustrating the principles of the present invention;

FIG. 2 is a left side view of the casting blank of FIG. 1;

FIG. 3 is a top view of the casting blank of FIG. 1;

FIG. 4 is a bottom view of the casting blank of FIG. 1;

FIG. 5 is a schematic cross-sectional view taken along lines 5—5 of FIG. 1;

FIG. 6 shows the casting blank of FIG. 1 as it would be applied in use to the forearm of a patient for support or splinting purposes;

FIG. 7 is a schematic showing of a mold for applying edge treatment material to a casting blank;

FIG. 8 is a more detailed cross-sectional view of one embodiment of the invention, showing the edge treatment;

FIG. 9 shows an embodiment of the invention in which an inner opening is provided with the anti-fraying edge treatment;

FIG. 10 shows an alternate edge treatment using a foaming material;

FIG. 11 shows a slab or strip of a casting material provided with the edge treatment; and FIG. 12 is a cross-sectional view taken along the plane indicated by the dashed line 12—12 of FIG. 11.

DETAILED DESCRIPTION OF THE PREFERRED EMBODIMENTS

Referring more particularly to the drawings, FIG. 1 shows a casting blank 12 having a main body area 14 which may be formed of spacer or double knit type material, and an edge treatment 16 of non-rigid bonding material. The additional views 2, 3 and 4 are side and end views of the casting blank of FIG. 1 which are included to show that the blank of FIG. 1 is substantially flat in its configuration.

With regard to the materials which may be employed, the casting or immobilization blank 12 could be formed of spacer or double knit type material as described hereinabove; or it may be formed of one or several layers of fiberglass or other high strength material. Following the application of the edge treatment 16 to the periphery of the casting blank 12, it may be impregnated with water hardenable material such as urethane. Alternatively, it may be impregnated with other types of hardenable material, including material which may be actuated by heat or by chemical reaction. The water hardenable urethane forms a very stiff and rigid construction and, in the absence of the edge treatment 16, it can result in hardening of the unraveled edges or filaments extending from the cut blank 12 causing irritation to the skin of the patient, after the casting blank has been dipped in water and applied to the portion of the anatomy requiring support or splinting.

The edge treatment 16 may be in the form of a non-water hardenable plastic such as a flexible urethane, or it may be in the form of other material such as silicone rubber, which is somewhat flexible in addition to being non-rigid and cushioning. In practice, the initial application of the edge treatment bonds the filaments and prevents the casting material from fraying when cut. As indicated in FIGS. 5 and 8, the edge treatment may form a bead along the edge of the casting blank which is cushioning or soft, and which may be resilient, and therefore does not scrape or irritate the skin of the patient at the edges of the cast.

FIG. 6 shows the blank 12 as applied to the forearm 18 of the user. Visible in FIG. 6 is the central area 14 of the casting blank, as well as the edge treatment 16 discussed above in connection with FIGS. 1–5. In addition, underlying the casting blank 12, is padding material such as the stockinette fabric 20. This stockinette material may be in the form of a sleeve. It is also possible to attach a padding type material to one or both sides of the casting material, and then apply the entire assembly to the anatomy, as shown in FIG. 12 and discussed hereinbelow. At the front of the cast, extending around the thumb 22, is a section of the cast 24 which has been optionally folded back upon itself to encircle the thumb 22, and to provide additional support and restraint.

It is noted that the configuration of the blank as shown in FIGS. 1 through 6 involves a broad lower area 23, a zone 25 of reduced cross-section to accommodate the bony protuberance on the reduced cross-section of the wrist, the wider portion 27 at the base of the hand, an additional reduced cross-section zone 29, and finally the enlarged area 24 for wrapping around and supporting the thumb. Incidentally, it is normally not folded back as shown in FIG. 6, but extends around the thumb without folding.

Referring now to FIG. 7 of the drawings, it includes a two-part mold having a lower section 32 and an upper section 34, which are hingedly mounted together by any suitable hinge construction 36 so that the upper portion 34 may fold down against the lower portion 32 of the mold. In practice, the edge treatment material may be applied entirely around the groove 38, and a rectangular piece of casting material laid over the lower portion 32 of the mold. Then the upper portion of the mold 34 is firmly folded down onto the lower portion of the mold 32, with the rib 40 pressing the fabric into the edge treatment material, so that it penetrates and bonds the filaments of the rectangular casting material.

Following this treatment, the rectangular casting material is trimmed by cutting through the sealed area 16, and the result is the irregularly shaped casting blank of FIG. 1 wherein the edge treatment bead forms the outer periphery of the casting blank 12. This technique of impregnating the edges of a casting blank can be used for other arrangements besides a shaped blank such as creating slabs or strips of casting material with sealed edges and ends.

As mentioned above, one preferred form for the main portion 14 of the casting blank is spacer or double knit type material, as shown in greater detail in FIG. 8 of the drawings. Double knit material is also disclosed in U.S. Pat. No. 5,284,031 granted Feb. 8, 1994. More specifically, returning to FIG. 8, the spacer material includes an upper woven or knit layer 52, a lower knit or woven layer 54, and a series of filaments 56 which serve to space apart the upper and lower layers 52 and 54 as well as providing a central matrix of fibers. The spacer assembly may be impregnated by water hardenable material, such as the water hardenable urethane, which is now widely used for casts and supports. The edge treatment 16 involves the impregnation of the periphery, or what will be the periphery of the irregularly shaped casting blank, by material 60, which extends from the edge into the casting blank for a very short distance forming the edge treatment 16. This avoids the fraying of the edges of the spacer material or other casting blank material which might otherwise create sharp edges or outwardly extending hardened filaments which would scrape and irritate the skin of the patient after hardening. Other types of casting material used to form a casting blank might include one layer of a single layer fabric composed of high strength fibers, multiple layers of this same fabric, or multiple layers of the preferred double knit type material.

Referring now to FIG. 9 of the drawings, it shows a casting blank 62 for the forearm, and including a thumb hole 64. The edge treatment as discussed hereinabove is provided both along the periphery 66 of the entire blank and around the thumb opening 64, as indicated by reference numeral 68.

FIG. 10 shows a casting blank 72 which may, for example, be formed of double knit material or other casting blank materials as discussed herein. A foam edge treatment 74 may be provided. One material which may be used is a two-part polyurethane foam available from Hastings Plastic Company, Santa Monica, Calif.

FIG. 11 shows a casting "slab" or strip 78 which may be a length of casting tape from a roll of casting tape, provided with the edge treatment 80 as discussed herein. As indicated in FIG. 12, taken as viewed along the plane identified by the dashed line 12—12 of FIG. 11, the casting "slab" or strip 78 may be made up of a series of layers 82 of casting material, which could be formed of fiberglass or other high strength fabrics. The lowermost layer 84 may be padding material such as a soft, closely woven fabric. The edge treatment 80 may serve to secure the multiple layers 82, 84 into a single unitary casting or splinting slab or tape section 78.

In conclusion, it is to be understood that the foregoing detailed description and the accompanying drawings relate to one preferred embodiment of the invention. Various alternatives and modifications may be employed without departing from the spirit and scope of the invention. Thus, by way of example and not of limitation, instead of using the mold as shown in FIG. 7, the casting blank may be cut to its intended final shape, and thereafter the edge treatment material may be applied to the edges of the blank. In addition, instead of using spacer material, also referenced as double knit type material, several layers of fiberglass or other high strength Casting material may be employed. It is also noted that the principles of the invention are applicable to casts for other portions of the body, such as the leg or upper arm, for specific examples. Concerning the edge treatment material, it may be formed of any material which is somewhat softer and less rigid, as well as being more cushioning than the hardenable urethane material forming the impregnation material for the body of the cast. Typical materials which may be used are silicone, rubber, adhesive, foam, TPE, vinyl, non-water hardenable urethane, and other plastic materials. The edge treatment material may be flexible, or it may be generally non-rigid and slightly softer than the water hardenable urethane material. It is also noted that, following preparation of the casting assembly, including impregnation with water hardenable material, the assembly may be sealed in a water vapor impermeable package until it is actually used for splinting or the like. With regard to the term "high strength filaments," reference is made to fiberglass, Keviar®, or aramids, for examples, and to materials having comparable high strength, as discussed in U.S. Pat. No. 6,139,513, granted Oct. 31, 2000, and in U.S. Pat. No. 6,186,966, granted Feb. 13, 2001. Accordingly, the present invention is not limited to the embodiment or embodiments shown in the drawings and described in detail hereinabove.

What is claimed is:

1. A method for forming an orthopaedic casting or immobilization blank or tape with sealed flexible edges comprising:

forming a sheet of double knit type spacer material with spaced upper and lower fabric layers and an open work matrix of filaments extending between and being integrally knit or woven into said upper and lower layers;

forming an immobilization blank or tape from said sheet of spacer material;

treating at least one edge of said spacer material by the application of non-rigid material to provide a non-irritating edge;

said treatment being at a concentration of more than 400 grams per square meter and at a level sufficient to significantly block subsequent impregnation of hardenable material into the edge of said immobilization blank; and impregnating at least a portion of said immobilization material with water hardenable material, with said prior edge treatment significantly blocking the water hardenable material from the treated edge.

2. A method as defined in claim 1 wherein the step of treating with non-rigid material utilizes a two-part mold with a groove in one part for receiving said material, and a mating rib in the other part of said mold to force the spacer material into said groove to impregnate the non-rigid material into the spacer material.

3. A method as defined in claim 2 wherein said spacer material initially extends outwardly beyond said groove, and wherein, following impregnation with the non-rigid material, the outer portions of the spacer material beyond the flexible material are trimmed off.

4. A method as defined in claim 1 further comprising the step of wetting the casting blank and applying it to that portion of the anatomy of a patient requiring splinting or support.

5. A method as defined in claim 1 wherein said treating and impregnating steps include blocking the water hardenable material from the edges of said blank, whereby the edges of said blank remain non-rigid following application of the blank onto a patient's anatomy, and these cushioning edges avoid irritation of the skin at the edges of the resultant cast or support.

6. A method as defined in claim 1 wherein the step of treating with non-rigid material involves initially treating said material along a narrow line defining a desired edge of the material, and cutting the material along said line.

7. A method as defined in claim 1 wherein the step of treating the edges of said blank with a non-rigid material secures at least one layer of padding type material to at least one side of said immobilization blank.

8. A method as defined in claim 1 further comprising the step of applying at least one layer of padding type material to at least one side of said blank.

9. A method for forming a casting blank, strip or tape with sealed edges comprising:
forming an extended area of at least one layer of casting fabric material;
treating at least one edge of said casting fabric material with non-rigid material to penetrate and seal the edges of the casting fabric material, said non-rigid material being applied in an amount between 400 and 10,000 grams per square meter; and at a level sufficient to significantly block subsequent impregnation of hardenable material into the edge of said immobilization blank; and
impregnating at least a portion of said casting fabric material with water hardenable material with said prior edge treatment significantly blocking the water hardenable material from the treated edge.

10. A method as defined in claim 9 wherein said treating and impregnating steps include blocking the water hardenable material from the edges of said casting fabric material, whereby the edges of said casting fabric material remain non-rigid following application of the fabric material onto a patient's anatomy, and these treated edges avoid irritation of the skin at the edges of the resultant cast or support.

11. A method as defined in claim 9 wherein said method includes forming said casting fabric material into the configuration of an irregularly shaped blank conforming to the portion of the anatomy requiring support or splinting.

12. A method as defined in claim 9 wherein said method includes treating with edge material which is flexible following solidification of the non-rigid material.

13. A method as defined in claim 9 wherein the step of treating the edges of said casting fabric material with non-rigid material uses a mold with a mating groove and rib configuration.

14. A method as defined in claim 9 wherein said casting fabric material is formed in an irregular configuration for application to the forearm of a patient.

15. A method as defined in claim 14 wherein said casting fabric material is applied to extend around the thumb of a patient.

16. A method as defined in claim 9 wherein said fabric material is formed at least in part of fiberglass.

17. A method as defined in claim 9 wherein said casting fabric material is formed in a tape configuration.

18. A method as defined in claim 9 wherein said casting fabric is formed in a strip configuration.

19. A method as defined in claim 9 wherein the step of treating the edges of said casting blank strip or tape with a non-rigid material secures at least one layer of padding type material to at least one side of said casting fabric material.

20. A method as defined in claim 9 further comprising the step of applying at least one layer of padding type material to at least one side of said casting fabric material.

21. A method of forming a splint for the forearm and thumb comprising:
forming an immobilization blank having a broad width area for extending around the forearm and wrist, a reduced width area following by an upper broadened area for encircling the thumb;
treating at least one edge of said blank to avoid sharp edges;
impregnating at least a portion of said casting blank with water hardenable material;
wetting said casting blank; and
applying said casting blank to the forearm of a patient with said upper broadened area encircling the thumb.

22. A method as defined in claim 21 wherein said immobilization blank is formed with two reduced width areas.

23. A method as defined in claim 21 wherein the step of treating the edges includes impregnating the edges with non-rigid material and at a level sufficient to significantly block subsequent impregnation of hardenable material into the edge of said immobilization blank.

24. A method as defined in claim 21 wherein at least one layer of padding type material is applied to at least one side of said immobilization blank.

25. A method as defined in claim 21 wherein the step of treating the edges of said immobilization blank secures at least one layer of padding type material to at least one side of said immobilization blank.

26. A method for forming a casting blank with sealed flexible edges comprising:
forming a sheet of double knit type spacer material with spaced upper and lower fabric layers and an open work matrix of filaments extending between and being integrally knit or woven into said upper and lower layers;
forming an immobilization blank from said sheet of spacer material;
treating the edges of said spacer blank with flexible material and at a level sufficient to significantly block subsequent impregnation of hardenable material into the edge of said immobilization blank; and
impregnating at least a portion of said casting blank with water hardenable material with said prior edge treatment significantly blocking the water hardenable material from the treated edge;
whereby the edges of said casting blank remain flexible following application of the casting blank onto a patient's anatomy, and these flexible edges avoid irritation of the skin at the edges of the cast.

27. A method as defined in claim 26 wherein the step of treating with flexible material utilizes a two-part mold with a groove in one part for receiving said flexible material, and a mating rib in the other part of said mold to force the spacer material into said groove to impregnate the flexible material into the spacer material.

28. A method as defined in claim 26 wherein said spacer material initially extends outwardly beyond said groove, and wherein, following treatment with the flexible material, the outer portions of the spacer material beyond the flexible material are trimmed off.

29. A method as defined in claim 26 wherein the step of treating the edges of said casting blank secures at least one layer of padding type material to at least one side of said casting blank.

30. A method as defined in claim 26 further comprising the step of applying at least one layer of padding type material to at least one side of said casting blank.

31. A method for forming an immobilization blank with sealed flexible edges comprising:
forming an assembly of at least one layer of casting fabric material;
forming an immobilization blank from said casting fabric material;
treating at least one edge of said casting blank with flexible material, said material being applied in an amount between 400 and 10,000 grams per square meter; and at a level sufficient to significantly block subsequent impregnation of hardenable material into the edge of said immobilization blank; and
impregnating at least a portion of said casting blank with water hardenable material with said prior edge treatment significantly blocking the water hardenable material from the treated edge.

32. A method as defined in claim 31 wherein said treating and impregnating steps include blocking the water hardenable material from the edges of said blank;
whereby the edges of said blank remain non-rigid following application of the blank onto a patient's anatomy, and these cushioning edges avoid irritation of the skin at the edges of the resultant cast or support.

33. A method as defined in claim 31 wherein the step of impregnating with flexible material utilizes a two-part mold with a groove in one part for receiving said flexible material, and a mating rib in the other part of said mold to force the casting fabric material into said groove to impregnate the flexible material into the casting fabric material.

34. A method as defined in claim 33 wherein said casting fabric material initially extends outwardly beyond said groove, and wherein, following impregnation with the cushioning material, the outer portions of the casting fabric material beyond the cushioning material are trimmed off.

35. A method as defined in claim 31 wherein the step of treating the edges of said immobilization blank secures at least one layer of padding type material to at least one side of said immobilization blank.

36. A method as defined in claim 31 further comprising the step of applying at least one layer of padding type material to at least one side of said immobilization blank.

37. An orthopaedic casting assembly comprising:
at least one layer of casting fabric material having edges;
non-rigid edge treatment material applied to at least one edge of said casting fabric material in an amount of between 400 and 10,000 grams per square meter, to avoid irritating the skin of the patient; and at a level sufficient to significantly block subsequent impregnation of hardenable material into the edge of said immobilization blank; and
water hardenable material impregnated into at least a portion of said casting fabric material with said prior edge treatment significantly blocking the water hardenable material from the treated edge.

38. A casting assembly as defined in claim 37 wherein said casting fabric material is formed of spacer material.

39. A casting assembly as defined in claim 37 wherein said casting material includes a substantial proportion of high strength fibers.

40. A casting assembly as defined in claims 37 wherein said casting fabric material includes multiple layers of fabric.

41. A casting assembly as defined in claim 40 wherein said edge treatment material holds said multiple layers together.

42. An orthopaedic casting assembly as defined in claim 37 wherein padding material is attached to at least one side of said assembly.

43. An orthopaedic casting assembly as defined in claim 37 wherein said casting material has an opening therethrough, and wherein the edges of said opening are treated with said edge treatment material.

44. An orthopaedic casting assembly as defined in claim 37 wherein said casting fabric material is in the form of an elongated strip and said edge treatment material is applied transversely to the length of said strip.

45. A casting assembly as defined in claim 37 wherein at least one layer of padding type material is secured to said casting fabric with the non-rigid edge treatment.

46. A casting assembly as defined in claim 37 wherein said casting fabric material is in the form of an irregularly shaped blank conforming to the portion of the anatomy requiring support or splint.

47. A method for forming an immobilization blank with sealed flexible edges comprising:
forming an assembly of at least one layer of casting fabric material;
forming an immobilization blank from said casting fabric material;
treating at least one edge of said casting blank with flexible material; and at a level sufficient to significantly block subsequent impregnation of hardenable material into the edge of said immobilization blank;
impregnating at least a portion of said casting blank with water hardenable material; with said prior edge treatment significantly blocking the water hardenable material from the treated edge;
said method further including attaching at least one layer of padding material to said casting fabric material by the flexible edge treatment material.

48. An orthopaedic casting assembly comprising:
at least one layer of casting fabric material having edges;
non-rigid edge treatment material applied to at least one edge of said casting fabric material to avoid skin irritation;
water hardenable material impregnated into at least a portion of said casting fabric material; and
at least one layer of padding type material being attached to said casting fabric material by said edge treatment material.

* * * * *